United States Patent [19]
Tornier

[11] Patent Number: 5,171,289
[45] Date of Patent: Dec. 15, 1992

[54] FEMORAL PROSTHESIS WITH CEMENT RETAINING SEAL

[75] Inventor: Alain Tornier, Crolles, France

[73] Assignee: Etablissements Tornier, Saint Ismier, France

[21] Appl. No.: 793,141

[22] Filed: Nov. 18, 1991

[30] Foreign Application Priority Data

Nov. 19, 1990 [FR] France .................. 90 14694

[51] Int. Cl.⁵ .................................. A61F 2/34
[52] U.S. Cl. .......................... 623/23; 623/16
[58] Field of Search ............. 623/22, 23, 18, 16

[56] References Cited

U.S. PATENT DOCUMENTS 4,997,448 3/1991 Filer ........................... 623/23

FOREIGN PATENT DOCUMENTS 0393425 10/1990 European Pat. Off. ........... 623/22

Primary Examiner—David Isabella
Attorney, Agent, or Firm—Dowell & Dowell

[57] ABSTRACT

A femoral prosthesis having a bore extending through the stem thereof and which includes a seal surrounding the stem adjacent the bore which acts under pressure of a cement introduced through the bore to seal the cement within the upper portion of the medullary canal of the femur.

6 Claims, 2 Drawing Sheets

FEMORAL PROSTHESIS WITH CEMENT RETAINING SEAL

BACKGROUND OF THE INVENTION

1. Field of the Invention

The present invention relates to a femoral element for a total hip prosthesis and more particularly to the means for fixing it in the medullary canal of the femur.

2. History of the Related Art

It is known that, up to the present time, three processes exist for fixing hip-joint endoprostheses, namely either by fixing with the aid of a cement, by direct impaction, i.e. the engagement by controlled force of the femoral stem in the medullary canal without using cement, or by partial fixation and solely in the upper part of the medullary canal as described in U.S. Pat. No. 4,888,022.

For femoral prostheses fixed via a cement, two methods exist for implementation:
the acrylic cement is simply placed in the medullary canal and the prosthesis is impacted;
a plug is placed in the medullary canal at about 1 cm beyond the end of the femoral stem, then cement is poured or injected in the canal and, finally, the stem is impacted in order to place the cement previously introduced under pressure. The excessive quantity of cement emerges via the upper end of the femur.

These cemented prostheses present certain drawbacks concerning the risks associated with the use of the cement and more particularly due to the rise in temperature and to a release of products which present a variable toxicity.

An immediate fixation is obviously obtained, but over the whole length of the stem without privileged zone, not taking into account the different zones of elasticity of the femur.

This zone of fixation changes the natural transmission of the stresses on the bone and, in the long run, modifies the osseous structures in the sense of deteriorating the fixation.

In the case of recovery, all the cement must be removed and, to that end, the plug of cement at the lower end of the prosthesis must be pierced, which is long and difficult work.

The femoral prostheses fixed without cement presents a surface appearance over all or part of the femoral stem so as to obtain an immediate stability in the medullary canal.

This method of fixation comprises certain drawbacks due to the tapering form of the stems of the prostheses, bringing about a very random contact in the metaphysal part of the femur and limited in the best cases to a few zones which cannot be foreseen. Moreover, the bone is subjected to stresses during fixation and to a considerable deterioration when the femoral prosthesis has to be withdrawn.

Finally, a micromobility may occur, bringing about a separation in the mean run.

The last process of fixation consists in a hip prosthesis of which the upper part is coated over the whole of its surface with an elastomer bladder. This bladder forms a retaining pouch upon introduction of a settable fluid. It inflates, applying against the inner walls of the medullary canal and more particularly in the diaphysal-metaphysal zone of the femur. Finally, the outer surface of the bladder comprises zones of rehabilitation of the bone which are disposed in a determined grid.

This method of fixation comprises certain drawbacks due to the operational stresses created by the introduction of a new element inside the medullary canal. Moreover, the elastomer bladder risks not being fluid-tight in its lower part under the effect of pressure during the introduction of the settable fluid. Finally, the positioning of this bladder on the body of the hip prosthesis considerably increases its cost price.

SUMMARY OF THE INVENTION

The improvements forming the subject matter of the present invention aim at overcoming the drawbacks set forth hereinabove and at producing a hip prosthesis whose femoral stem is cemented only in its upper part, the lower, non-cemented part determining by an appropriate profile an acceptable, easy, axial guiding of the prosthesis.

To that end, the stem of the prosthesis according to the invention comprises an oblique bore whose origin lies at the junction of the joining piece with respect to the femoral stem and which opens out at the level of the median part of the element, in the diaphysalmetaphysal zone of the femur; a seal intended to retain an acrylic cement which is introduced in the oblique bore until it overflows in the upper part of the medullary canal; and means for retaining the seal located below the opening end of the bore.

BRIEF DESCRIPTION OF THE DRAWINGS

The accompanying drawings, given by way of example, will enable the invention, the characteristics that it presents and the advantages that it is capable of procuring, to be more readily understood.

DESCRIPTION OF THE PREFERRED EMBODIMENT

Figure 1:
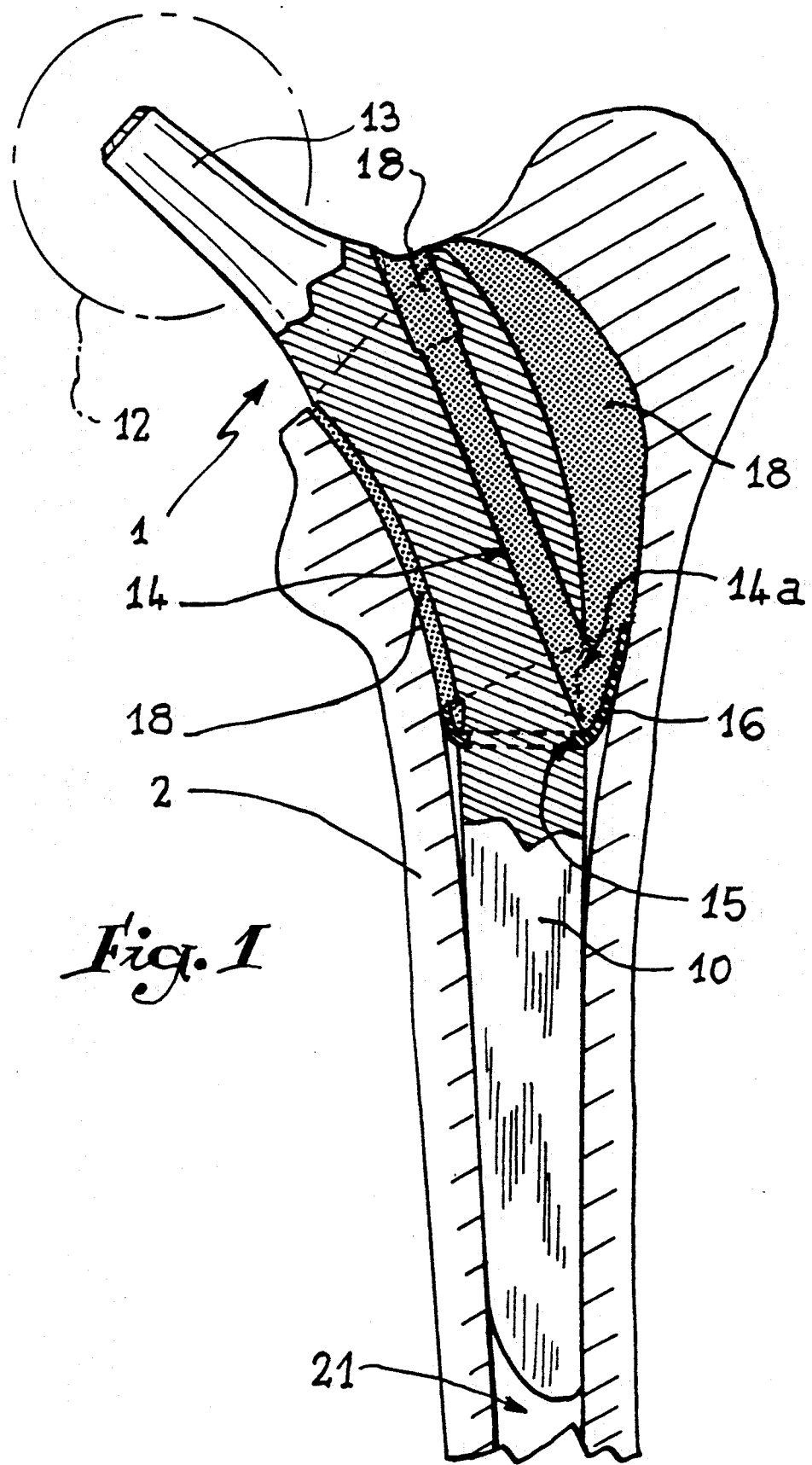
FIG. 1 is a longitudinal section showing the femoral prosthesis according to the invention, introduced and sealed in the medullary canal of a femur.

FIG. 1 shows the femoral element 1 of a hip prosthesis which is intended to be placed inside the medullary canal 21 of a femur 2.

Element 1 comprises a stem 10 and an inclined joining piece 13 supporting at its free end a cephalic head or ball 12 illustrated in broken lines and forming with the cotyloid prosthesis the joint of the femur with respect to the hip bone.

Figure 2:
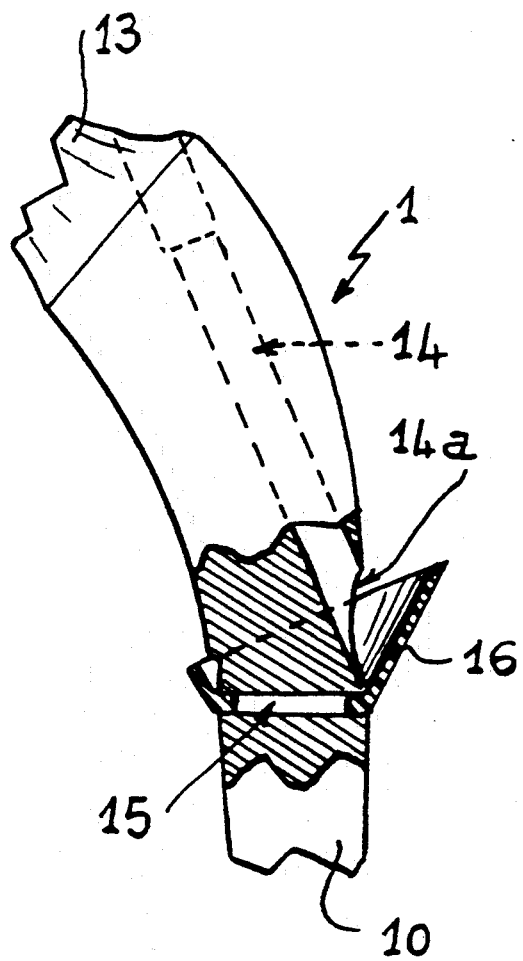
FIG. 2 is a partial side view with parts broken away, illustrating the positioning of the seal which retains the cement.

The stem 10 of element 1 is provided for example with an oblique bore 14 of any inclination traversing right through it so as to open out in the median zone of the stem and opposite the joining piece 13, as shown in FIGS. 1 and 2.

Figure 3:
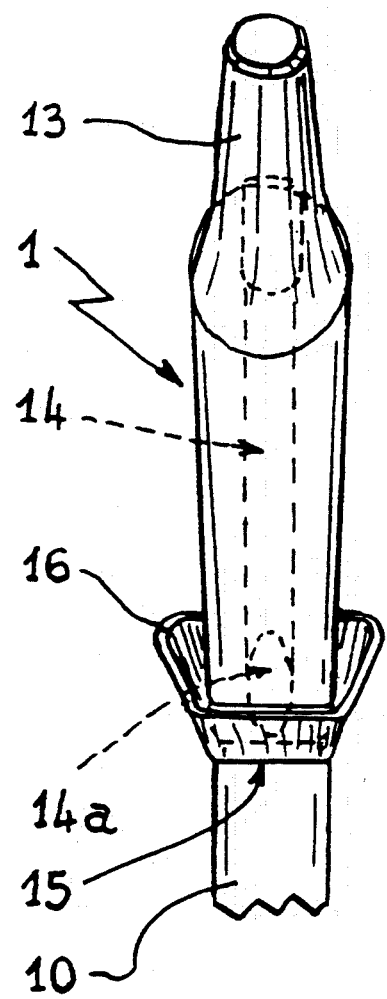
FIG. 3 is a partial front view of the femoral element of FIG. 1.

According to the invention, depending on the patient's morphology, a groove 15 is made for example in the median part of the periphery of the stem 10 just below the lowermost opening end of the oblique bore 14 (FIGS. 2 and 3). Groove 15 allows a dish- or collar-shaped seal 16 to be positioned so that its concavity faces the inclined joining piece 13. This seal is asymmetrical, i.e. its uppermost oblique part lies towards the lowermost opening end 14a of the bore 14 (FIGS. 2 and 3).

During positioning of the femoral stem 10 inside the medullary canal 21, the seal is compressed in the centripetal direction and comes against the wall of the canal. Once the stem is in definitive position therein, the seal 16 provides tightness between the upper part and the lower part of the medullary canal 21 of the femur 2.

The femoral element 1 is fixed by introducing an acrylic cement 18 inside the oblique bore 14, making it possible to bring the cement into contact under pressure with the seal 16, so that the latter inflates until it is forced against the walls of the medullary canal 21. The cavity determined above the seal 16 between the prosthesis and the medullary canal 21 of the femur 2 is then filled with the acrylic cement 18 until it overflows in the upper part of the canal, and flows back via the upper end of the oblique bore 14.

To that end, any other means might be used for injecting the acrylic cement 18 directly in the upper part of the medullary canal 21, for example a suitable syringe, bore 14 in that case being unnecessary.

The retaining seal 16 may be made either of a silastic (sic.) material which, due to its composition, perfectly follows the walls of the medullary canal 21, or of polyethylene or a bio-resorbable material.

This method of partial fixation makes it possible to obtain a prosthesis 1 having a perfect axial stability since the lower part of the stem 10 is placed without cement 18 in the corresponding part of the medullary canal 21, while the few degrees of freedom of the stem in the upper part of said canal are eliminated by the cement 18 which ensures a solid, immediate fixation of the prosthesis.

The fact of filling the medullary canal 21 only in its upper part around stem 10 clearly reduces the quantity of cement and diminishes the risks of toxicity and overheating. Similarly, the invention allows a considerable improvement in the work time during revision of a prosthesis, since the supply of the cement 18 at the moment of withdrawing the femoral prosthesis, is effected very easily once the femoral stem has been removed.

It goes without saying that the grooves 15 allowing positioning of the retaining seal 16 may be replaced by any other means, for example by wedging or gluing, without changing the scope of the invention.

I claim:

1. In a femoral prothesis which includes a femoral stem and an inclined joining piece for receiving a cephalic ball, the stem having a medial portion, the improvement comprising, an oblique bore extending from an upper opening generally between the joining piece and the stem through said stem to a lower opening in the medial portion of the stem, an asymmetrical retaining seal surrounding the stem adjacent said lower opening therein, said seal having a base portion and an oblique generally concave lip oriented toward said bore, said lip having an uppermost edge portion in generally opposing relationship to said lower opening, and means for retaining said base portion of said seal in engagement with said stem.

2. The femoral prothesis of claim 1 in which said means to retain said base portion of said seal includes a groove formed in the medial portion of the stem, said base portion of said seal being seated within said groove.

3. The femoral prothesis of claim 2 in which said seal is constructed of a material selected from a group of flexible materials consisting of plastics and bio-resorbable materials.

4. The femoral prothesis of claim 1 in which said seal is constructed of a material selected from a group of flexible materials consisting of plastics and bio-resorbable materials.

5. In a femoral prothesis which includes a femoral stem and an inclined joining piece for receiving a cephalic ball, the stem having a medial portion, the improvement comprising, a continuous groove formed in the medial portion of the stem, a retaining seal surrounding the medial portion of said stem, said seal having a base portion and a generally concave annular lip oriented toward said inclined joining piece, and said base portion of said seal being seated in engagement with said groove.

6. The femoral prothesis of claim 5 including an oblique bore extending between an upper opening generally between the stem and the inclined joining piece and a lower opening in the medial portion of the stem, said lip of said seal being oriented in opposing relationship to said lower opening.

* * * * *